(12) United States Patent
Neufeld et al.

(10) Patent No.: US 10,932,480 B2
(45) Date of Patent: Mar. 2, 2021

(54) ANIMAL FEED ADDITIVE CONTAINING DIURNOSID AND/OR CESTRUMOSID

(71) Applicant: Klaus Neufeld, Heiligenkreuz (AT)

(72) Inventors: Klaus Neufeld, Heiligenkreuz (AT); Nina Neufeld, Heiligenkreuz (AT)

(73) Assignee: Klaus Neufeld, Heiligenkreuz (AT)

( * ) Notice: Subject to any disclaimer, the term of this patent is extended or adjusted under 35 U.S.C. 154(b) by 0 days.

(21) Appl. No.: 16/073,691

(22) PCT Filed: Jan. 27, 2017

(86) PCT No.: PCT/EP2017/051744
§ 371 (c)(1),
(2) Date: Jul. 27, 2018

(87) PCT Pub. No.: WO2017/129732
PCT Pub. Date: Aug. 3, 2017

(65) Prior Publication Data
US 2019/0021367 A1    Jan. 24, 2019

(30) Foreign Application Priority Data
Jan. 29, 2016 (AT) .................................. 50049/2016

(51) Int. Cl.
| | |
|---|---|
| *A23K 10/30* | (2016.01) |
| *A23K 20/111* | (2016.01) |
| *A23K 20/163* | (2016.01) |
| *A23K 50/75* | (2016.01) |
| *A23K 50/30* | (2016.01) |
| *A23K 20/10* | (2016.01) |
| *A23K 20/174* | (2016.01) |
| *A61K 31/70* | (2006.01) |

(52) U.S. Cl.
CPC .............. *A23K 10/30* (2016.05); *A23K 20/10* (2016.05); *A23K 20/111* (2016.05); *A23K 20/163* (2016.05); *A23K 20/174* (2016.05); *A23K 50/30* (2016.05); *A23K 50/75* (2016.05); *A61K 31/70* (2013.01)

(58) Field of Classification Search
CPC ..... A23K 10/30; A23K 20/163; A23K 20/174
See application file for complete search history.

(56) References Cited

FOREIGN PATENT DOCUMENTS

| | | | |
|---|---|---|---|
| AT | 509 728 A1 | 11/2011 | |
| CN | 104366017 B | 8/2015 | |
| EP | 2 070 523 A1 | 6/2009 | |
| EP | 2 070 524 A1 | 6/2009 | |
| GB | 841273 * | 7/1960 | ............. A23K 10/30 |
| WO | 95/25522 A1 | 9/1995 | |
| WO | 2006/107451 A2 | 10/2006 | |
| WO | 2007/066355 A1 | 6/2007 | |
| WO | 2008/006582 A1 | 1/2008 | |
| WO | 2013/0432529 A1 | 3/2013 | |

OTHER PUBLICATIONS

Kosina (Food and Chemical Technology; 42, 2004, 85-91).*
Ahmad et al., "A Tigogenin Pentasaccharide from *Cestrum diurnum*," *Phytochemistry* 34(2):511-513, 1993. (6 pages).

* cited by examiner

*Primary Examiner* — Pancham Bakshi
(74) *Attorney, Agent, or Firm* — Seed IP Law Group LLP

(57) ABSTRACT

The invention relates to an animal feed additive containing a protein kinase C inhibitor selected from diurnoside, cestrumoside and mixtures thereof.

10 Claims, 7 Drawing Sheets

ANIMAL FEED ADDITIVE CONTAINING DIURNOSID AND/OR CESTRUMOSID

The invention relates to an animal feed additive for inhibiting protein kinase C.

Osteochondrosis/dyschondroplasia and leg weakness are common joint diseases that are responsible for high economic losses in broilers, laying hens, chickens, fattening pigs, breeding sows, ruminants but also cause high treatment costs in horses and dogs. The exact causes of osteochondrosis/dyschondroplasia and leg weakness have not yet been clearly defined, but in the most common cases, the consequence in all animal species is deformation of the bone with subsequent paralysis. These problems occur in particular with animals that experience a very rapid growth.

In practice, osteochondrosis/dyschondroplasia and leg weakness are treated with moderate success using so-called nonsteroidal anti-inflammatory drugs, which include, for example, acetylsalicylic acid, which is used in large quantities in poultry and swine in particular. However, this active ingredient must not be used for laying hens and lactating cows. For other farm animals, there are so-called withdrawal periods for nonsteroidal anti-inflammatory drugs, i.e., the active ingredient must not be administered for a certain period of time prior to slaughter of the animals. However, experience has shown that the problems associated with osteochondrosis/dyschondroplasia and leg weakness occur in particular at the end of the fattening period when the animals have already reached a high body weight. This period of time often overlaps with the withdrawal period. Basically, agriculture and lawmakers have attempted to reduce the use of drugs in farm animals. Therefore, from an economic standpoint, there is a demand for active ingredients that are capable of preventing the development of osteochondrosis/dyschondroplasia and leg weakness because by the time the changes have manifested, economic losses are already substantial.

Urolithiasis is a pathological process that occurs especially commonly in poultry, resulting in deposition of mineral complexes in the area of the urogenital tract. Urolithiasis results in an obstruction of the efferent urinary tract and in most cases also results in renal dysfunction. The economic importance of urolithiasis is substantial in laying hens in particular because, on one hand, it can result in a reduced laying output, while, on the other hand, it can also lead to an elevated mortality rate.

It has surprisingly been found that administering an animal feed additive/animal feed containing a plant-based inhibitor of protein kinase C (PKC inhibitor) selected from diurnoside, cestrumoside and mixtures thereof results in a definite reduction in occurrence of osteochondrosis/dyschondroplasia and leg weakness. It has surprisingly also been found that administering such an animal feed additive/animal feed leads to a definite reduction in the incidence of urolithiasis, in particular in commercial poultry.

Therefore, in one aspect, the invention relates to an animal feed additive for use for prevention of dyschondroplasia, osteochondrosis and/or leg weakness or for prevention of urolithiasis in farm animals, domestic animals and pets, where the animal feed additive contains a protein kinase C inhibitor selected from diurnoside, cestrumoside and mixtures thereof.

Based on the fact that the active ingredients diurnoside and cestrumoside are quite expensive, there has been a search for substances that will permit an economical use of diurnoside and cestrumoside. Difference substances have been tested as part of various experimental series.

It has surprisingly been found that the amount of diurnoside and cestrumoside to be used can be reduced while still achieving the same effect with regard to bioavailability, for example, if these active ingredients are used in combination with one or more optional ingredients selected from magnolol, honokiol and mixtures thereof, fungus mycelium of *Aspergillus niger*, fungus mycelium of *Aspergillus oryzae* and chelerythrin. With the help of the aforementioned optional ingredients, attempts to reduce the effective dose of cestrumoside and diurnoside by more than half have been successful. This procedure permits economical use in practice.

In one embodiment, the invention therefore relates to an animal feed additive containing the active ingredient selected from diurnoside, cestrumoside and mixtures thereof in combination with one or more additional ingredients selected from magnolol, honokiol and mixtures thereof, fungus mycelium of *Aspergillus niger*, fungus mycelium of *Aspergillus oryzae* and chelerythrin.

In one embodiment of the invention the animal feed additive contains the active ingredient selected from diurnoside, cestrumoside and mixtures thereof in combination with magnolol and/or honokiol.

In another embodiment, the animal feed additive contains the active ingredient selected from diurnoside, cestrumoside and mixtures thereof in combination with fungus mycelium of *Aspergillus niger* or *Aspergillus oryzae*.

In another embodiment the animal feed additive contains the active ingredient selected from diurnoside, cestrumoside and mixtures thereof in combination with chelerythrin.

The PKC inhibitor contained in the animal feed additive according to the invention plus optional ingredients also present may be of natural or synthetic origin. A PKC inhibitor or optional ingredient of natural origin may be present, for example, in the form of plant-based materials and/or plant extracts. The plant extracts can be produced by known methods, such as solid-liquid extraction with water, hot water or steam or with organic solvents, such as ethanol or methanol or solvent mixtures or mixtures of such solvents with water or by extraction with supercritical $CO_2$ as the extraction medium. The extraction is preferably carried out at temperatures in the range of 20° C. to 160° C. The extracts are adjusted to the desired active ingredient content by mixing individual batches or by mixing with inert vehicle substance. The active ingredient contents are analyzed by means of HPLC.

According to one embodiment, the animal feed additive contains the PKC inhibitor selected from diurnoside, cestrumoside and mixtures there in combination with vitamin $D_3$ metabolites, preferably selected from calcifediol and calcitriol. The ratio between the PKC inhibitor and vitamin $D_3$ metabolites is preferably in the range of 1:1000 to 1000:1, more preferably in the range of 1:100 to 100:1.

The animal feed additive according to the invention comprises the PKC inhibitor selected from diurnoside and/or cestrumoside, optionally used in combination with one or more additional ingredients selected from magnolol, honokiol and mixtures thereof, fungus mycelium of *Aspergillus niger*, fungus mycelium of *Aspergillus oryzae* and chelerythrin, together with an excipient to facilitate dosing of the active ingredient. For example, this excipient can be selected from vegetable or mineral excipients such as a powdered feed, middlings, grass meal, plant-based green meals, bran, clay minerals, zeolites, silicates, etc.

The PKC inhibitor selected from diurnoside, cestrumoside and mixtures thereof is preferably present in the animal feed additive according to the invention in a dose of 0.1 mg to 20,000 mg, more preferably 1 mg to 1000 mg per kg animal feed additive.

The dose of magnolol and/or honokiol in the animal feed additive according to the invention is preferably in the range of 0.5 g to 50 g per kg animal feed additive.

The dose of fungus mycelium of *Aspergillus niger* or *Aspergillus oryzae* in the animal feed additive according to the invention is preferably in the range of 500,000 mg to 999,999.9 mg/kg animal feed additive.

The dose of chelerythrin in the animal feed according to the invention is preferably in the range of 0.1 g to 10 g per kg animal feed additive.

The invention also relates to an animal feed comprising an animal feed additive as described above for use for prevention of dyschondroplasia, osteochondrosis and/or leg weakness or for prevention of urolithiasis in farm animals, domestic animals and pets together with at least one feed component selected from the group consisting of protein sources, carbohydrate sources, roughage, silage, fats, vitamins, minerals and trace elements.

The animal feed according to the invention contains the PKC inhibitor selected from diurnoside, cestrumoside and mixtures thereof, preferably in a dose of 0.0001 mg to 3 mg per kilogram of feed, based on a feed with 88% dry solids. Higher doses are possible and effective but make it expensive to use this additive in feed.

In other embodiments, the animal feed according to the invention contains the PKC inhibitor selected from diurnoside, cestrumoside and mixtures thereof in combination with one or more optional ingredients selected from magnolol, honokiol and mixtures thereof, fungus mycelium of *Aspergillus niger*, fungus mycelium of *Aspergillus oryzae* and chelerythrin.

The dose of magnolol and/or honokiol in the animal feed is preferably in the range of 0.1 mg to 10 mg per kg feed, preferably in the range of 0.3 mg to 3 mg per kg feed (based on feed with 88% dry solids).

The dose of fungus mycelium of *Aspergillus niger* or *Aspergillus oryzae* in the animal feed is preferably in the range of 50 mg to 5000 mg per kg feed, more preferably in the range of 200 to 2000 mg per kg feed (based on feed with 88% dry solids).

The dose of chelerythrin in the animal feed is preferably in the range of 0.05 mg to 5 mg per kg feed (based on feed with 88% dry solids).

The invention also relates to a premix for preparing an animal feed. The premix contains an animal feed additive according to the invention together with at least one feed component selected from the group consisting of protein carriers, carbohydrate carriers, roughage, silage, fats, vitamins, minerals and trace elements.

According to another feature, the invention relates to the use of a protein kinase C inhibitor selected from diurnoside and/or cestrumoside, in an animal feed additive or in a drinking water additive for prevention of dyschondroplasia, osteochondrosis and/or leg weakness or for prevention of urolithiasis in farm animals, domestic animals and pets. The protein kinase C inhibitor is preferably administered to the animal in an amount of 0.00001 mg to 0.3 mg per kilogram of body weight per day.

The invention also relates to the use of a protein kinase C inhibitor selected from diurnoside and/or cestrumoside in combination with one or more optional ingredients selected from magnolol, honokiol and mixtures thereof, fungus mycelium of *Aspergillus niger* or *Aspergillus oryzae* and chelerythrin in an animal feed additive or drinking water additive for prevention of dyschondroplasia, osteochondrosis and/or leg weakness or for prevention of urolithiasis in farm animals, domestic animals and pets.

Magnolol and/or honokiol is/are preferably administered to the animal in a dose of 0.004 mg to 1 mg per kilogram of body weight per day.

Fungus mycelium of *Aspergillus niger* or *Aspergillus oryzae* is administered to the animal preferably in an amount of 2 mg to 500 mg per kilogram of body weight per day.

Chelerythrin is preferably administered to the animal in an amount of 0.002 mg to 0.5 mg per kilogram of body weight per day.

The animal feed additive according to the invention may also be a drinking water additive. The expedient amounts of active ingredients and optional ingredients for administration may correspond to the amounts per kilogram of body weight per day indicated above.

The invention also relates to the use of a protein kinase C inhibitor selected from diurnoside and cestrumoside, optionally in combination with one or more optional ingredients selected from magnolol, honokiol and mixtures thereof, fungus mycelium of *Aspergillus niger* or *Aspergillus oryzae* and chelerythrin, for producing an animal feed additive or an animal feed or an animal feed premix or a drinking water additive for use for prevention of dyschondroplasia, osteochondrosis and/or leg weakness or for prevention of urolithiasis in farm animals, domestic animals and pets.

The invention is explained in greater detail below on the basis of examples with reference to the figures, in which FIG. 1 shows the incidence of osteochondrosis in feeding experiments with broilers using animal feed additives according to the invention in comparison with the null hypothesis control group, a control group with calcitriol and a control group with calcifediol;

EXAMPLES

Example 1

In a commercial boiler feeding operation, five stalls each with approximate 43,000 animals were compared with regard to the incidence of osteochondrosis/dyschondroplasia in a field test. All the stalls were fed using conventional boiler fattening feed, distributed under the brand name GeflügelmastKorn® (Company: Garant Tiernahrung [Garant Animal Nutrition]), wherein no further additives were used in stall K1 (controls).

For stall K2 (control group calcitriol), a feed additive containing 20 ppm calcitriol in an amount of 150 ppm (based on feed with 88% dry solids) was mixed into the broiler fattening feed.

For stall K2 (control group calcifediol), a feed additive containing 200 ppm calcifediol in an amount of 150 ppm (based on feed with 88% dry solids) was mixed into the broiler fattening feed.

For stall V1 (experimental group with diurnoside plus calcitriol), the feed additive according to the invention, containing 100 ppm diurnoside and 10 ppm calcitriol was mixed into the boiler fattening feed in an amount of 150 ppm (based on feed with 88% dry solids).

For the stall V2 (experimental group with cestrumoside plus calcifediol), the feed additive according to the invention, containing 20 ppm cestrumoside and 100 ppm calcifediol in an amount of 150 ppm (based on feed with 88% dry solids) was mixed into the broiler fattening feed.

Figure 1:
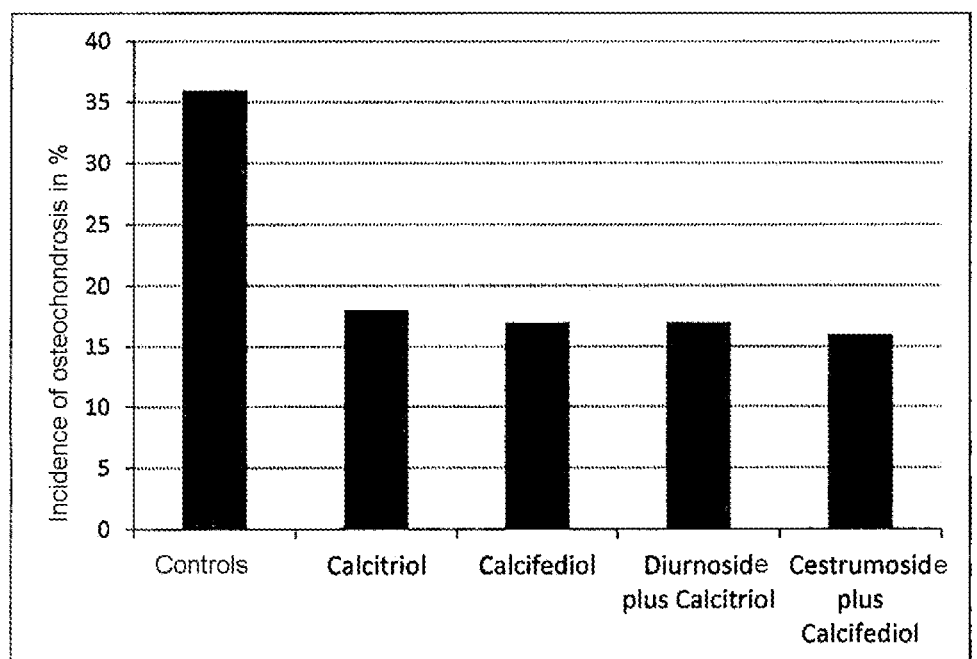

The experiment began when the animals were placed in stalls on day 1 of life and it ended with slaughter of the animals on day 30. After the slaughter, 100 slaughtered bodies were taken randomly from each stall. Pathological tests for osteochondrosis were performed on these 500 slaughtered bodies. The results are shown in FIG. 1. It can be seen from FIG. 1 that the animal feed additive according to the invention was capable of significantly reducing the incidence of osteochondrosis/dyschondroplasia in a broiler fattening operation under conventional production conditions. In addition, it can be seen that the effective doses for calcitriol and calcifediol could be reduced by one-half. In the respective operation, it was found that, when using the experimental substances, the mobility of the animals was much better than that in the null hypothesis control group.

Example 2

In a commercial boiler fattening operation, five stalls with approximately 43,000 animals each were compared with respect to the incidence of osteochondrosis/dyschondroplasia and urolithiasis in a field test. All stalls were given feed in the form of conventional broiler fattening feed, distributed under the brand name GeflügelmastKorn® (Company: Garant Tiernahrung [Garant Animal Nutrition]), wherein no additional additives were used in stall K (controls).

For the stall V1 (experimental group diurnoside), the feed additive according to the invention, containing 100 ppm diurnoside in an amount of 150 ppm (based on feed with 88% dry solids) was mixed into the broiler fattening feed.

For the stall V2 (cestrumoside experimental group) the feed additive according to the invention, containing 20 ppm cestrumoside in an amount of 150 ppm (based on feed with 88% dry solids) was mixed into the broiler fattening feed.

For the stall V3 (experimental group diurnoside plus magnolol/honokiol), the feed additive according to the invention, containing 100 ppm diurnoside and 2% mixture consisting of magnolol/honokiol (magnolol/honokiol in a 2:1 ratio) in an amount of 50 ppm (based on feed with 88% dry solids) was mixed into the broiler fattening feed.

For the stall V4 (cestrumoside experimental group plus magnolol/honokiol), the feed additive according to the invention, containing 20 ppm cestrumoside and 2% of a mixture consisting of magnolol/honokiol (magnolol/honokiol in a 2:1 ratio) in an amount of 50 ppm (based on feed with 88% dry solids) was mixed into the broiler fattening feed.

Figure 2:
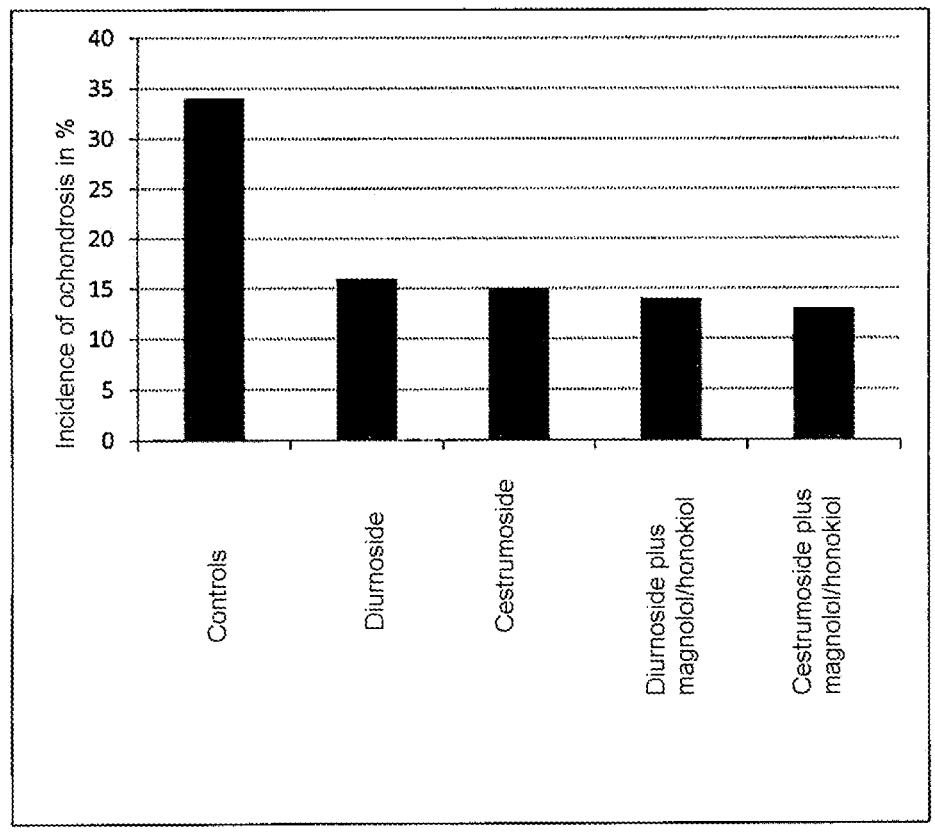
FIG. 2 shows the incidence of osteochondrosis in feeding experiments with broilers using animal feed additives according to the invention in comparison with the control group.
Figure 3:
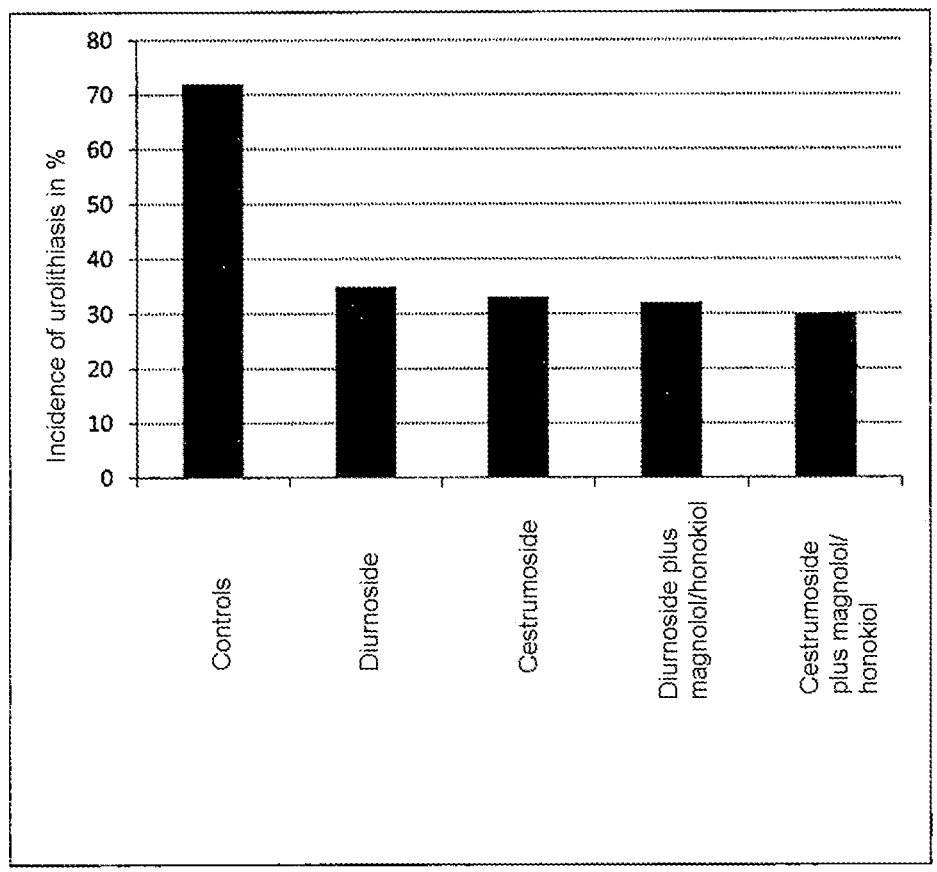
FIG. 3 shows the incidence of urolithiasis in feeding experiments with broilers using animal feed additives according to the invention in comparison with the control group.

The experiment started when the animals were placed in the stall on day 1 of life and it ended with slaughter of the animals on day 30 of life. After the slaughter, 100 slaughtered bodies were randomly removed from each stall. Pathological tests for osteochondrosis and urolithiasis (macroscopically detectable formation of urinary stones) were performed on these 500 slaughtered bodies. The results are shown in FIGS. 2 and 3. It can be seen from FIG. 2 that the animal feed additive according to the invention was capable of significantly reducing the incidence of osteochondrosis/dyschondroplasia in a broiler fattening operation under conventional production conditions. In the respective operation, it was found that the mobility of the animals was significantly better than that in the control group when using the test substances. It can be seen from FIG. 3 that the animal feed additive according to the invention was capable of significantly reducing the incidence of urolithiasis in a broiler fattening operation under conventional production conditions.

Example 3

Five stalls each with approx. 43,000 animals in a commercial broiler fattening operation were compared with respect to the incidence of osteochondrosis/dyschondroplasia and urolithiasis in a field test. All the animals in the stalls were fed a conventional commercial broiler fattening feed distributed under the brand name GeflügelmastKorn® (Company: Garant Tiernahrung [Garant Animal Nutrition]), wherein no additional additives were used in stall K (controls).

For the stall V1 (experimental group diurnoside plus *Aspergillus niger*), the feed additive according to the invention, containing 10 ppm diurnoside and 90% mycelium from *Aspergillus niger* in an amount of 500 ppm (based on feed with 88% dry solids) was mixed into the broiler fattening feed.

For the stall V2 (cestrumoside experimental group plus *Aspergillus oryzae*) the feed additive according to the invention, containing 2 ppm cestrumoside and 90% mycelium of *Aspergillus oryzae* in an amount of 500 ppm (based on feed with 88% dry solids) was mixed into the broiler fattening feed.

For the stall V3 (experimental group diurnoside plus chelerythrin) the feed additive according to the invention, containing 100 ppm diurnoside and 1% chelerythrin in an amount of 50 ppm (based on feed with 88% dry solids) was mixed into the broiler fattening feed.

For the stall V4 (cestrumoside experimental group plus chelerythrin), the feed additive according to the invention, containing 20 ppm cestrumoside and 1% chelerythrin in an amount of 50 ppm (based on feed with 88% dry solids) was mixed into the broiler fattening feed.

Figure 4:
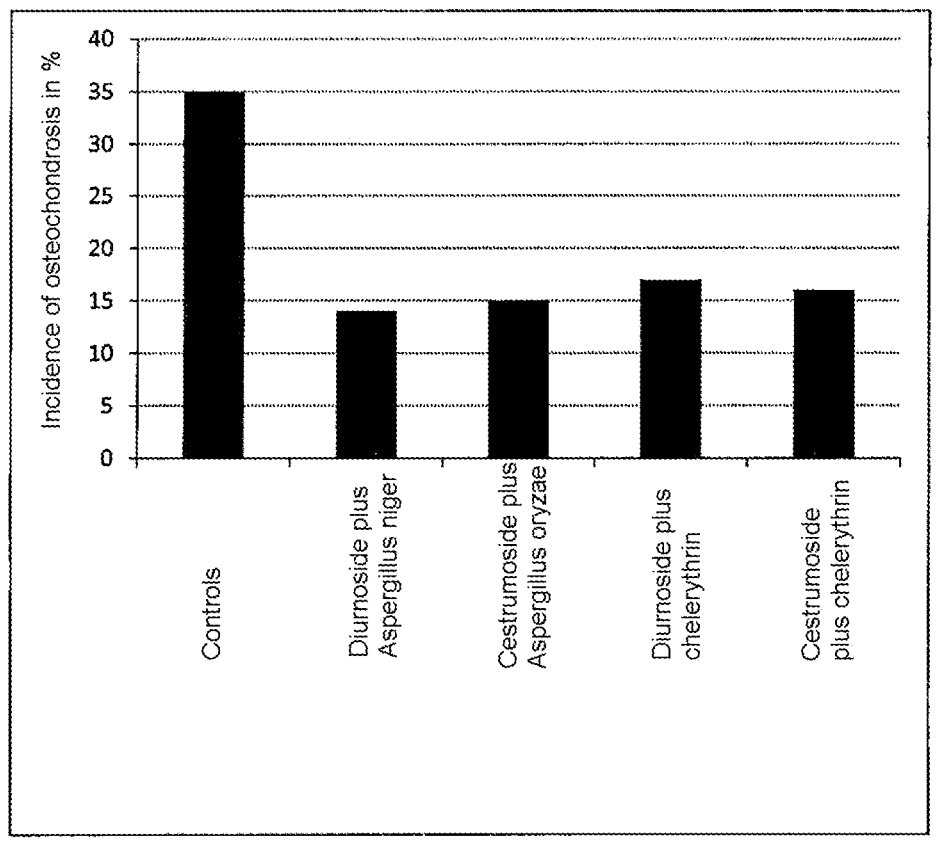
FIG. 4 shows the incidence of osteochondrosis in feeding experiments with broilers using animal feed additives according to the invention in comparison with the control group.
Figure 5:
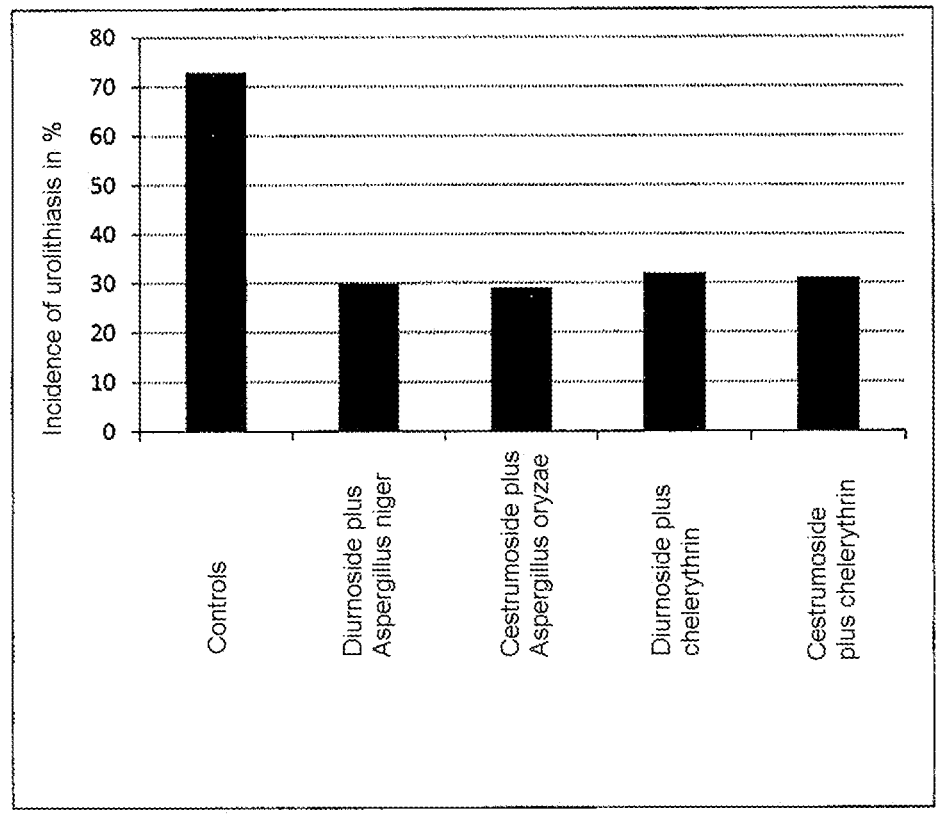
FIG. 5 shows the incidence of urolithiasis in feeding experiments with broilers using animal feed additives according to the invention in comparison with the control group.

The experiment started when the animals were placed in the stall on day 1 of life and it ended with slaughter of the animals on day 30 of life. After the slaughter, 100 slaughtered bodies were randomly removed from each stall. Pathological tests for osteochondrosis and urolithiasis were performed on these 500 slaughtered bodies. The results are shown in FIGS. 4 and 5. It can be seen from FIG. 4 that the animal feed additive according to the invention was capable of significantly reducing the incidence of osteochondrosis/dyschondroplasia in a broiler fattening operation under the conventional production conditions. In the respective operation it was found that the mobility of the animals was significantly better when using the test substances than in the control group. It can be seen from FIG. 5 that the animal feed additive according to the invention was capable of significantly reducing the incidence of urolithiasis in a broiler fattening operation under the usual production conditions.

Example 4

Three stalls each with approximately 43,000 animals in a commercial broiler fattening operation were compared with respect to the incidence of osteochondrosis/dyschondroplasia and urolithiasis in a field test. All the animals in the stalls were fed a conventional commercial broiler fattening feed distributed under the brand name GeflügelmastKorn® (Company: Garant Tiernahrung [Garant Animal Nutrition]), but no additional additives were used in stall K (controls).

For the stall V1 (experimental group diurnoside plus cestrumoside plus magnolol/honokiol plus *Aspergillus niger*), the feed additive according to the invention, containing 10 ppm diurnoside, 2 ppm cestrumoside, 1000 ppm of a mixture consisting of magnolol/honokiol (magnolol/honokiol in a 2:1 ratio) and 90% mycelium from *Aspergillus niger* in an amount of 500 ppm (based on feed with 88% dry solids) was mixed into the broiler fattening feed.

For the stall V2 (experimental group diurnoside plus cestrumoside plus *Aspergillus oryzae*) the feed additive according to the invention, containing 10 ppm diurnoside, 2 ppm cestrumoside and 90% mycelium of *Aspergillus oryzae* in an amount of 500 ppm (based on feed with 88% dry solids) was mixed into the broiler fattening feed.

Figure 6:
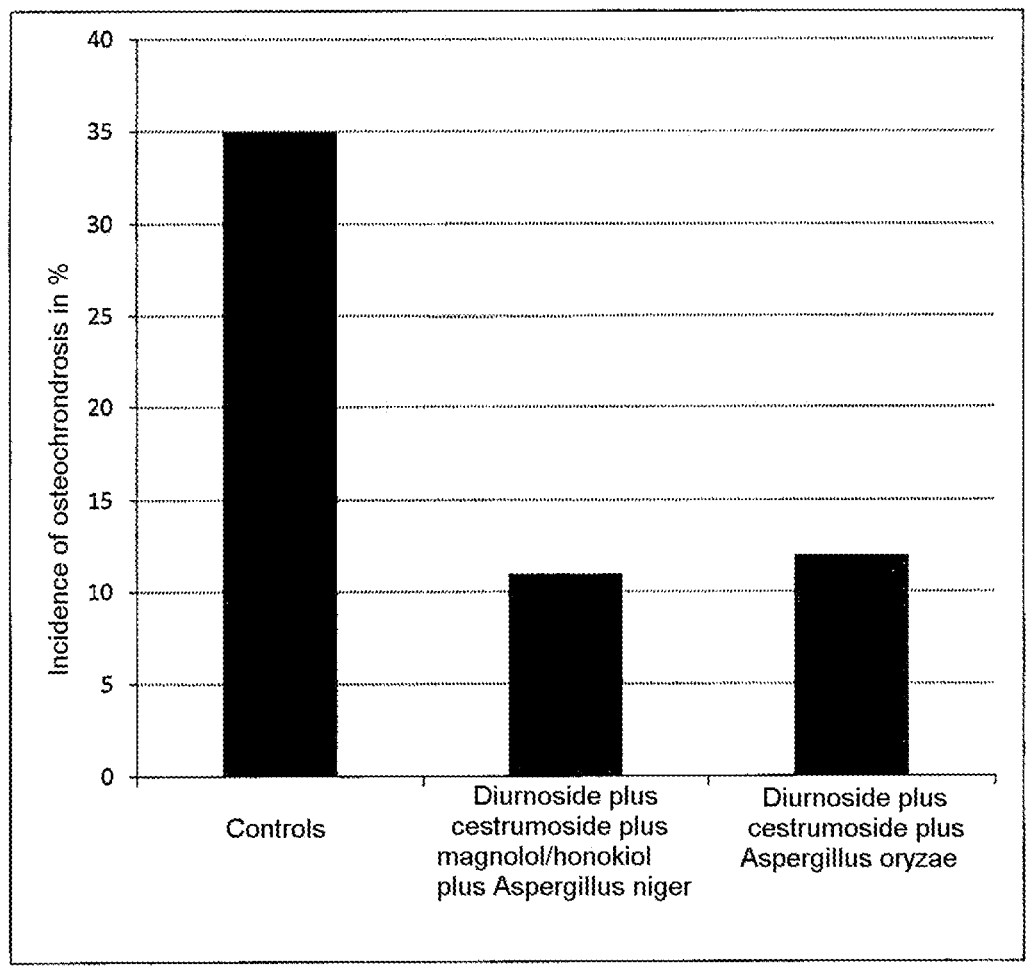
FIG. 6 shows the incidence of osteochondrosis in feeding experiments with broilers using the animal feed additives according to the invention in comparison with the control group.
Figure 7:
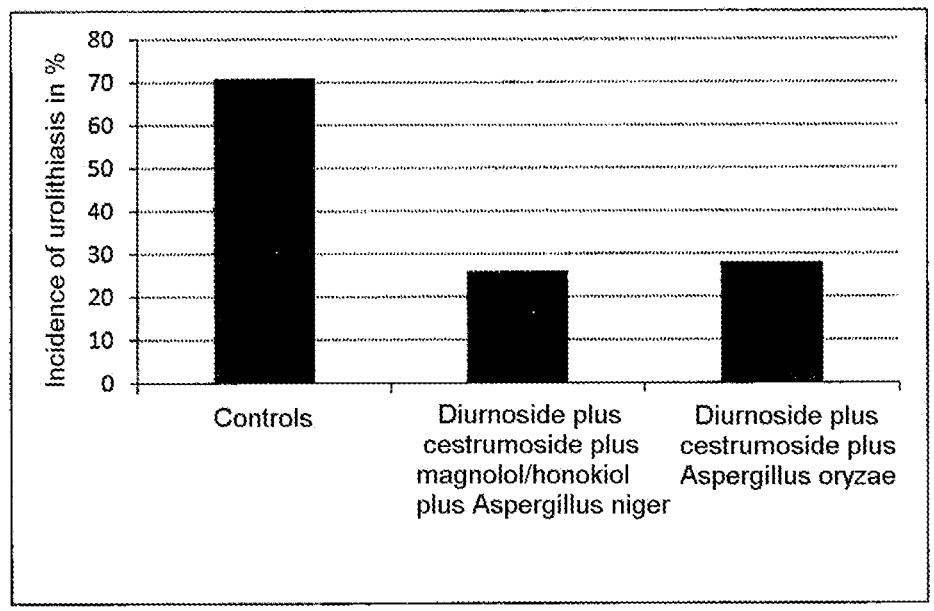
FIG. 7 shows the incidence of urolithiasis in feeding experiments with laying hens using the animal feed additives according to the invention in comparison with the control group.

The experiment started when the animals were placed in the stall on day 1 of life and it ended with slaughter of the animals on day 30 of life. After the slaughter, 100 slaughtered bodies were randomly removed from each stall. Pathological tests for osteochondrosis and urolithiasis (macroscopically discernible formation of urinary stones) were performed on these 300 slaughtered bodies. The results are shown in FIGS. 6 and 7. It can be seen from FIG. 6 that the animal feed additive according to the invention was capable of significantly reducing the incidence of osteochondrosis/dyschondroplasia in a broiler fattening operation under the conventional production conditions. In the respective operation it was found that the mobility of the animals was significantly better when using the test substances than in the control group. It can be seen from FIG. 7 that the animal feed additive according to the invention was capable of significantly reducing the incidence of urolithiasis in a broiler fattening operation under the usual production conditions.

Example 5

Four groups of laying hens each with 50 animals per group were compared with respect to the incidence of leg weakness in one experimental stall. All the experimental groups were fed commercial laying hen feed, distributed under the brand name LegeKorn® (Company: Garant Tiernahrung [Garant Animal Nutrition]), wherein no additional additives were used in the feed for the control group.

For experimental group 1, a feed additive according to the invention, containing 100 ppm diurnoside in an amount of 150 ppm (based on feed with 88% dry solids) was mixed into the exclusive laying feed.

For experimental group 2, a feed additive according to the invention, containing 20 ppm cestrumoside in an amount of 150 ppm (based on feed with 88% dry solids) was mixed into the exclusive laying feed.

For experimental group 3, a feed additive according to the invention, containing 50 ppm diurnoside and 10 ppm cestrumoside in an amount of 150 ppm (based on feed with 88% dry solids) was mixed into the exclusive laying feed.

Figure 8:
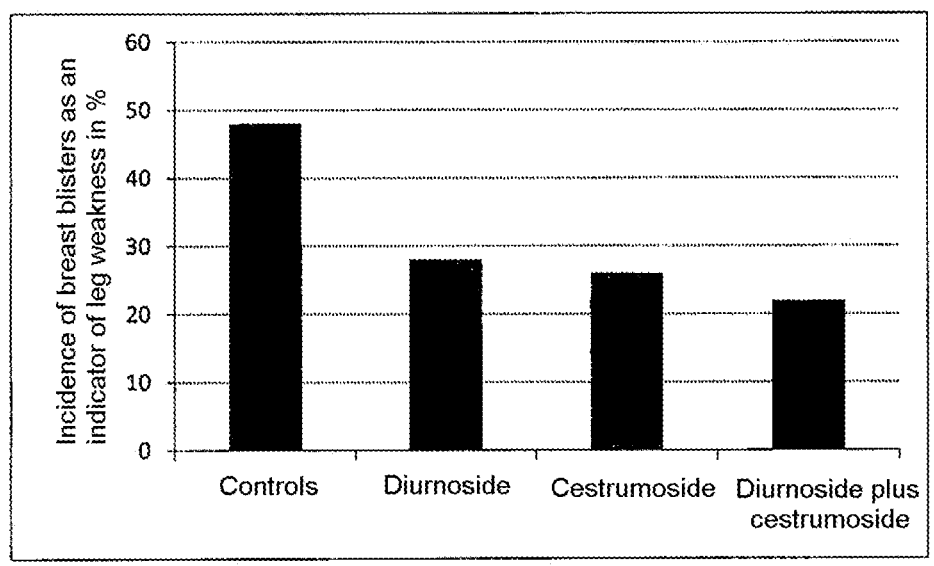
FIG. 8 shows the incidence of breast blisters as an indicator of leg weakness in feeding experiments with laying hens using the animal feed additives according to the invention in comparison with the control group.

The experiment began in week 19 of life of the animals. The animals were kept on the ground in four sections with straw as bedding material. The egg laying nests were separated and also furnished with straw as bedding material. The experiment ended with slaughter of the animals after 15 months. After the slaughter, all the slaughtered bodies subjected to a macroscopic pathological examination for breast blisters. A cyst between the chest bone and the skin above it caused by increased laying on the chest area was classified as a breast blister. Since this type of laying occurs more commonly in poultry with leg weakness than in healthy animals, the incidence of breast blisters was used as an indicator of restricted mobility and therefore leg weakness. The results of this experiment are shown in FIG. 8. FIG. 8 shows that when using the respective experimental substance, the incidence of breast blisters as an indicator of leg weakness was reduced significantly in comparison with the control group.

Example 6

Five groups of male fattening pigs with 20 animals per group in an experimental stall were compared with respect to the incidence of osteochondrosis. The animals were placed in stalls with an average weight of 30 kg per group. All the experimental groups were fed a conventional pig fattening feed distributed under the brand name SchweinemastKorn® OGT (Company: Garant Tiernahrung [Garant Animal Nutrition]) wherein no additional additives were used in the feed in the control group.

For experimental group 1, a feed additive according to the invention, containing 100 ppm diurnoside in an amount of 100 ppm (based on feed with 88% dry solids) was mixed into the pig fattening feed.

For experimental group 2, a feed additive according to the invention, containing 20 ppm cestrumoside in an amount of 100 ppm (based on feed with 88% dry solids) was mixed into the pig fattening feed.

For experimental group 3, a feed additive according to the invention, containing 10 ppm diurnoside and containing 90% mycelium of *Aspergillus oryzae* in an amount of 500 ppm (based on feed with 88% dry solids) was mixed into the pig fattening feed.

For experimental group 4, a feed additive according to the invention, containing 2 ppm cestrumoside and containing 90% mycelium of *Aspergillus niger* in an amount of 500 ppm (based on feed with 88% dry solids) was mixed into the pig fattening feed.

Figure 9:
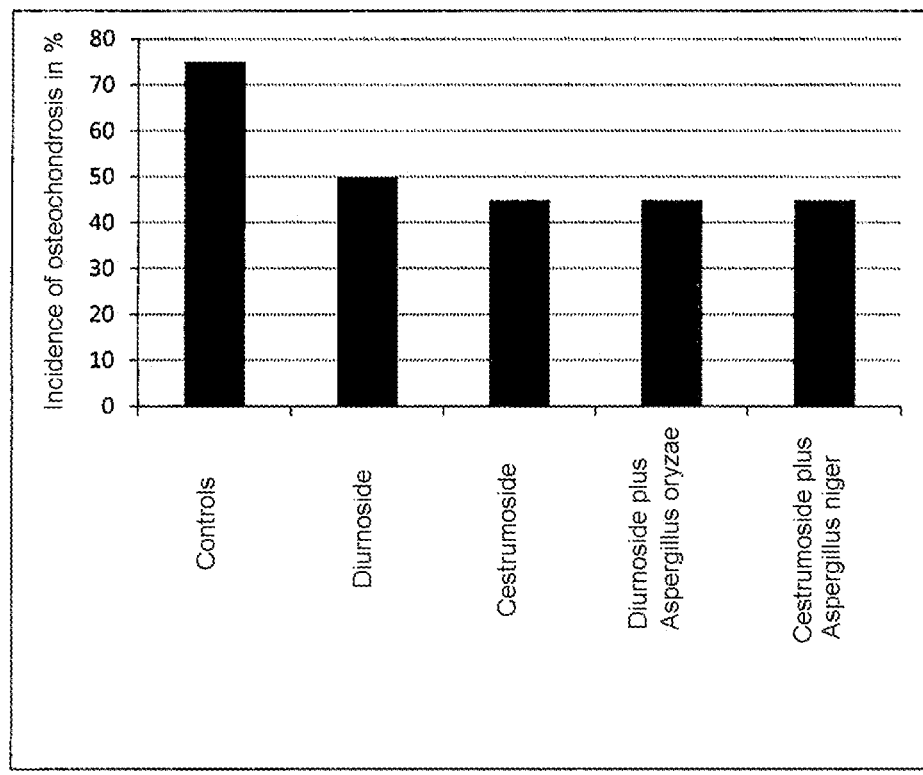
FIG. 9 shows the incidence of osteochondrosis in feeding experiments with fattening pigs using the animal feed additives according to the invention in comparison with the control group.

The animals were fattened up to an average weight of 100 kg per group. The experiment ended with slaughter of the animals. After the slaughter, the right knee joint (*Articulatio genus*) of each slaughtered body was subjected to a macroscopic pathological examination for osteochondrosis. FIG. 9 illustrates the results of this experiment. FIG. 9 shows that the incidence of osteochondrosis of the right knee joint using the substances according to the invention was significantly lower than in the control group. In all the experimental groups, fewer animals with mobility problems (sitting) were observed.

Example 7

In one experimental stall three groups of male fattening pigs with 20 animals per group were compared with respect to the incidence of osteochondrosis. The animals were kept in stalls with an average weight of 30 kg per group. All experimental groups were fed commercial pig fattening feed distributed under the brand name SchweinemastKorn® OGT (Company: Garant Tiernahrung [Garant Animal Nutrition]), wherein additional additives were used in the feed for the control group.

For experimental group 1, a feed additive according to the invention, containing 100 ppm diurnoside and 10 ppm calcifediol in an amount of 100 ppm (based on feed with 88% dry solids) was mixed into the pig fattening feed.

For experimental group 2, a feed additive according to the invention, containing 20 ppm cestrumoside and 10 ppm calcitriol in an amount of 100 ppm (based on feed with 88% dry solids) was mixed into the pig fattening feed.

Figure 10:
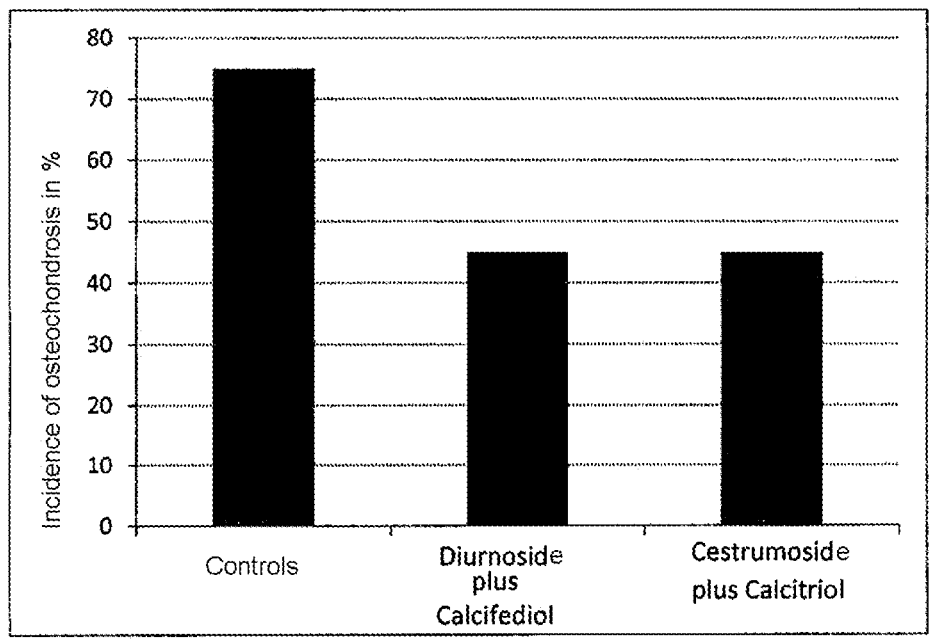
FIG. 10 shows the incidence of osteochondrosis in feeding experiments with fattening pigs using the animal feed additives according to the invention in comparison with the control group.

The animals were fattened up to an average weight of 100 kg per group. The experiment ended with the slaughter of the animals. After the slaughter the right knee joint (*Articulatio genus*) of each slaughtered body was subject to a macroscopic pathological examination for osteochondrosis. FIG. 10 illustrates the results of this experiment. FIG. 10 shows that the animal feed additive according to the invention led to a significant reduction in the incidence of osteochondrosis in fattening pigs.

The invention claimed is:

1. An animal feed, comprising:
   (a) at least one feed component selected from protein sources, carbohydrate sources, roughage, silage, fats, vitamins, minerals and trace elements; and
   (b) an animal feed additive for protein kinase C inhibition, said additive comprising an active ingredient selected from diurnoside, cestrumoside and mixtures thereof, wherein said active ingredient is present in a dose of 0.0001 mg to 3 mg per kilogram of feed based on feed with 88% dry solids.

2. The animal feed of claim 1 in which the animal feed additive further comprises at least one second ingredient that is selected from (i) magnolol, (ii) honokiol, (iii) fungus mycelium from *Aspergillus niger*, (iv) fungus mycelium from *Aspergillus oryzae*, and (v) chelerythrin.

3. The animal feed of claim 2, wherein the at least one second ingredient is either one or both of magnolol and honokiol.

4. The animal feed of claim 2, wherein the at least one second ingredient is either one or both of fungus mycelium of *Aspergillus niger* and fungus mycelium of *Aspergillus oryzae*.

5. The animal feed of claim 1 in which the animal feed additive further comprises a vitamin $D_3$ metabolite that is selected from calcifediol and calcitriol.

6. The animal feed of claim 5 in which (i) the active ingredient of the animal feed additive for protein kinase C inhibition and (ii) the vitamin $D_3$ metabolite are present at a ratio of 1:1000 to 1000:1, or are present at a ratio of 1:100 to 100:1.

7. A method for reducing incidence of one or more of dyschondroplasia, osteochondrosis, leg weakness, or urolithiasis in an animal that is selected from a farm animal, a domestic animal, and a pet, comprising administering to the animal the animal feed of claim 1.

8. The method of claim 7, wherein the active ingredient selected from diurnoside, cestrumoside and mixtures thereof is administered to the animal in an amount of 0.00001 mg to 0.3 mg per kilogram of body weight per day.

9. The method of claim 7, wherein the incidence of one or more of dyschondroplasia, osteochondrosis, leg weakness, or urolithiasis is reduced in the animal, relative to the incidence in an animal that does not receive said animal feed.

10. The method of claim 9, wherein the active ingredient selected from diurnoside, cestrumoside and mixtures thereof is administered to the animal in an amount of 0.00001 mg to 0.3 mg per kilogram of body weight per day.

* * * * *